(12) United States Patent
Knies et al.

(10) Patent No.: US 8,716,511 B2
(45) Date of Patent: May 6, 2014

(54) PROCESS FOR PREPARING ORGANOALKOXYHYDROSILANES

(75) Inventors: Wolfgang Knies, Burghausen (DE); Karin Bögershausen, Burghausen (DE)

(73) Assignee: Wacker Chemie AG, Munich (DE)

(*) Notice: Subject to any disclaimer, the term of this patent is extended or adjusted under 35 U.S.C. 154(b) by 118 days.

(21) Appl. No.: 13/380,337

(22) PCT Filed: Jun. 21, 2010

(86) PCT No.: PCT/EP2010/058694
§ 371 (c)(1),
(2), (4) Date: Dec. 22, 2011

(87) PCT Pub. No.: WO2010/149603
PCT Pub. Date: Dec. 29, 2010

(65) Prior Publication Data
US 2012/0095248 A1     Apr. 19, 2012

(30) Foreign Application Priority Data
Jun. 26, 2009   (DE) .......................... 10 2009 027 257

(51) Int. Cl.
C07F 7/10     (2006.01)

(52) U.S. Cl.
USPC ........... 556/413; 556/470; 556/478; 556/479; 556/481

(58) Field of Classification Search
USPC ........................ 556/470, 413, 478, 479, 481
See application file for complete search history.

(56) References Cited

U.S. PATENT DOCUMENTS

| | | | |
|---|---|---|---|
| 3,642,851 A | 2/1972 | Bennett | |
| 4,224,040 A | 9/1980 | Gazzarrini et al. | |
| 5,136,072 A | 8/1992 | Shinohara et al. | |
| 2001/0044551 A1* | 11/2001 | Childress et al. | ............. 556/413 |
| 2005/0054211 A1 | 3/2005 | Xu et al. | |
| 2006/0241272 A1 | 10/2006 | Geisberger | |
| 2007/0287849 A1 | 12/2007 | Mayorga et al. | |
| 2010/0274028 A1 | 10/2010 | Mueh et al. | |
| 2011/0184205 A1 | 7/2011 | Rauleder et al. | |

FOREIGN PATENT DOCUMENTS

| | | |
|---|---|---|
| DE | 1 964 553 A1 | 7/1970 |
| DE | 1964553 A1 | 7/1970 |
| EP | 0223210 A2 | 5/1987 |
| GB | 994076 A | 6/1965 |
| GB | 1050308 A | 12/1966 |
| JP | 54119420 A2 | 9/1979 |
| JP | 1125390 A2 | 5/1989 |
| JP | 4321694 A2 | 11/1992 |
| JP | 10036377 A2 | 2/1998 |
| JP | 2002173495 A2 | 6/2002 |
| JP | 2006306874 A2 | 11/2006 |
| JP | 2007269679 A2 | 10/2007 |
| JP | 2008050341 A2 | 3/2008 |
| JP | 2012511529 T2 | 5/2012 |
| WO | 2008087072 A1 | 7/2008 |
| WO | WO-2008/087072 * | 7/2008 ................ C07F 7/20 |
| WO | 2009049943 A1 | 4/2009 |

OTHER PUBLICATIONS

Richter, Herbert, International Search Report dated Oct. 28, 2010, for PCT Application No. EP2010/058694.
English language patent abstract corresponding to JP 1-125390 A2, published May 17, 1989.
English language patent abstract corresponding to JP 2007-269679 A2, published Oct. 18, 2007.
English language patent abstract corresponding to JP 10036377 A2, published Feb. 10, 1998.
English language patent abstract corresponding to JP 2002173495 A2, published Jun. 21, 2002.

* cited by examiner

*Primary Examiner* — Kamal Saeed
*Assistant Examiner* — Janet L Coppins
(74) *Attorney, Agent, or Firm* — RatnerPrestia

(57) ABSTRACT

Process for preparing organoalkoxyhydrosilanes with a boron content less than 100 ppb and of the formula $$R^1_x H_y Si(OR^2)_z$$

where x+y+z=4 and x, y, z are greater than or equal to 1, wherein, in a first step, a boron-contaminated organohalohydrosilane of the formula $$R^1_x H_y SiHal_z$$

where x+y+z=4, x, y, z are greater than or equal to 1, and $R^1$ are linear or branched alkyl, cycloalkyl, aryl, alkenyl or arylalkyl radicals having 1 to 12 carbon atoms and Hal is F, Cl, Br or I, is subjected to a treatment with silica or aluminosilicate and the silica or the aluminosilicate is subsequently removed from the organohalohydrosilane in a second step and then the purified organohalohydrosilane is reacted with alcohol $R^2$—OH where $R^2$ is a methyl, ethyl, n-propyl, isopropyl, n-butyl, isobutyl, tert-butyl, n-pentyl, isopentyl, neopentyl or tert-pentyl radical.

7 Claims, No Drawings

PROCESS FOR PREPARING ORGANOALKOXYHYDROSILANES

CROSS REFERENCE TO RELATED APPLICATIONS

This application is the national phase filing of international patent application No. PCT/EP2010/058694, filed 21 Jun. 2010, and claims priority of German patent application number 10 2009 027 257.7, filed 26 Jun. 2009, the entireties of which applications are incorporated herein by reference.

FIELD OF THE INVENTION

The invention relates to a process for preparing organoalkoxyhydrosilanes, and to organohalohydrosilanes.

BACKGROUND OF THE INVENTION

Commercially available organohalohydrosilanes are contaminated with boron, which is often troublesome in products which are produced therefrom, such as preferably electronic components.

There is a known process for purifying alkoxysilanes (EP 223210, 13, Nov. 1986, Toray), in which an alkoxysilane is heated in the presence of a purifying agent (acid clay or metal halide) and treated with a neutralizing agent, and the alkylalkoxysilane is removed from neutralization by-products and excess neutralizing agent (chlorine reduction).

SUMMARY OF THE INVENTION

It is an object of the invention to improve upon the state of the art and more particularly to provide organoalkoxyhydrosilanes which contain a minimum level of boron.

DETAILED DESCRIPTION OF THE INVENTION

The invention provides a process for preparing organoalkoxyhydrosilanes with a boron content less than 100 ppb and of the formula $$R^1_x H_y Si(OR^2)_z$$

where x+y+z=4 and x, y, z are greater than or equal to 1, wherein, in a first step, a boron-contaminated organohalohydrosilane of the formula $$R^1_x H_y SiHal_z$$

where x+y+z=4, x, y, z are greater than or equal to 1, and $R^1$ are linear or branched alkyl, cycloalkyl, aryl, alkenyl or arylalkyl radicals having 1 to 12 carbon atoms and Hal is F, Cl, Br or I, is subjected to a treatment with silica or aluminosilicate and the silica or the aluminosilicate is subsequently removed from the organohalohydrosilane in a second step and then the purified organohalohydrosilane is reacted with alcohol $R^2$—OH where $R^2$ is a methyl, ethyl, n-propyl, isopropyl, n-butyl, isobutyl, tert-butyl, n-pentyl, isopentyl, neopentyl or tert-pentyl radical.

$R^1$ is preferably linear or branched alkyl, cycloalkyl, aryl, alkenyl or arylalkyl radicals, preferably alkyl radicals. The $R^1$ radicals preferably have 1 to 12 and especially 1 to 6 carbon atoms. Particularly preferred $R^1$ radicals are methyl, ethyl, n-propyl, isopropyl, n-butyl, isobutyl, tert-butyl, n-pentyl, isopentyl, neopentyl or tert-pentyl radical and phenyl radical.

Preferred organoalkoxyhydrosilanes are alkylalkoxyhydrosilanes, and preferred alkylalkoxyhydrosilanes are dimethoxymethylsilane and diethoxymethylsilane, particular preference being given to diethoxymethylsilane. Preferred organohalohydrosilanes are alkylhalohydrosilanes, and preferred alkylhalohydrosilanes are dimethylchlorosilane and dichloromethylsilane, particular preference being given to dichloromethylsilane.

Preferred alcohols $R^2$—OH are those in which $R^2$ is a methyl, ethyl, n-propyl, isopropyl, n-butyl, isobutyl, tert-butyl, n-pentyl, isopentyl, neopentyl or tert-pentyl radical and phenyl radical, particular preference being given to those with the methyl, ethyl, butyl, n-propyl, isopropyl radical.

The lower amount of the alcohol arises from the stoichiometry, i.e. 2 mol of alcohol per mole of organohalohydrosilane. Preference is given to a 50% molar excess, particular preference to a 30% molar excess.

It is optionally possible with preference to use, as well as the alcohol, solvents such as preferably aliphatic solvents, such as isohexane, pentane, octane, decane, aromatic solvents such as toluene, xylene, preference being given to using isohexane, pentane and decane, particular preference to using isohexane, in the process according to the invention.

Preference is given to equal molar amounts of solvent and organohalohydrosilane, particular preference to between 0.6 and 1 mol of solvent per mole of organohalohydrosilane.

Particular preference is given to nonpolar solvents, in order to lower the solubility of hydrochlorides.

It is optionally possible with preference to use acid scavengers, such as preferably amines, such as ethylenediamine, isopropylamine, triisopropylamine, urea, preference being given to urea.

The lower limit for the acid scavenger is one equivalent of acid scavenger per equivalent of organohalohydrosilane, preference being given to a 30% molar excess, particular preference to a 5 to 10% molar excess.

In the process according to the invention, optionally solvent, alcohol and optionally acid scavenger are initially charged in a flask with stirrer, reflux condenser and dropping funnel; the dropping funnel is used to add organohalohydrosilane dropwise in pure form or in solution. After the addition has ended, reaction is continued for a few hours, the lower phase is removed and discarded, the upper phase is optionally neutralized with metal hydrogencarbonate and filtered, the solvent is optionally drawn off and the organoalkoxyhydrosilane is optionally fractionally distilled.

Before use, the organohalohydrosilane is subjected to the inventive purification step. In this step, the organohalohydrosilane is treated with aluminosilicate, preferably perlite, preferably 0.1 to 50% by weight, more preferably 1 to 20% by weight, especially preferably 5 to 15% by weight, based on the organohalohydrosilane, for preferably 1 h to 20 h, preferably under nitrogen, preferably at 25° C. up to the boiling point of the organohalohydrosilane and standard pressure (1.01325 bar) while stirring, and then a filtration or a distillation (preferably no return stream, preferably standard pressure (1.01325 bar)), preferably at a top temperature corresponding to the boiling point of the organohalohydrosilane, is undertaken.

In a further preferred purification step, the organohalohydrosilane is treated with silica, preferably precipitated silica, preferably 0.1 to 50% by weight, more preferably 1 to 20% by weight, especially preferably 5 to 15% by weight, based on the organohalohydrosilane, for preferably 1 h to 20 h, preferably under nitrogen, preferably at 25° C. up to the boiling point of the organohalohydrosilane and standard pressure (1.01325 bar) while stirring, and then a filtration is undertaken.

As the purification step, organohalohydrosilane is more preferably purified by treatment with aluminosilicate and subsequent simple distillation.

An upper limit in the boron content is preferably less than 100 ppb (1 ppb=$10^{-9}$=0.000000001), in an order of emphasis going from preferred to more preferred a boron content of less than 90 ppb, 80 ppb, 70 ppb, 60 ppb, 50 ppb, 40 ppb, 30 ppb, 20 ppb, 10 ppb, 5 ppb, 1 ppb, 0.1 ppb, more preferably less than 0.01 ppb, of boron. In addition, a lower limit in the boron content in an order of emphasis going from preferred to less preferred is more than 0.01 ppb, 0.1 ppb, 1.0 ppb, 5 ppb, 10 ppb, 20 ppb, 30 ppb, 40 ppb, 50 ppb, 60 ppb, 70 ppb, 80 ppb, 90 ppb, preferably less than 100 ppb.

Ratios of Silica or Aluminosilicate to Organohalohydrosilane:

Preferably 0.1 to 50% by weight, based on organohalohydrosilane used, more preferably 1 to 20% by weight, especially preferably between 5 and 15% by weight.

Treatment Temperature:

Preferably −80° C. to +100° C., preferably above 0° C., more preferably +15 to +45° C.

The upper limit is the boiling point of the organohalohydrosilane at standard pressure (1.01325 bar).

Treatment Pressure

Standard pressure (1.01325 bar) to 3 bar, preferably standard pressure (1.01325 bar)

Distillation Pressure 0.1 mbar to standard pressure (1.01325 bar), preferably standard pressure (1.01325 bar)

The invention further provides an organoalkoxyhydrosilane of the formula

$R^1_x H_y SiOR^2_z$ where x+y+z=4 x, y, z are greater than or equal to 1 and $R^1$ are linear or branched alkyl, cycloalkyl, aryl, alkenyl or arylalkyl radicals having 1 to 12 carbon atoms, and $R^2$ is a methyl, ethyl, n-propyl, isopropyl, n-butyl, isobutyl, tert-butyl, n-pentyl, isopentyl, neopentyl or tert-pentyl radical and phenyl radical, characterized in that it has a boron content of less than 100 ppb.

Preferred alkylalkoxyhydrosilanes are dimethoxymethylsilane and diethoxymethylsilane, particular preference being given to diethoxymethylsilane.

The invention further provides an organohalohydrosilane of the formula

$R^1_x H_y SiHal_z$ where x+y+z=4 x, y, z are greater than or equal to 1 and $R^1$ are linear or branched alkyl, cycloalkyl, aryl, alkenyl or arylalkyl radicals having 1 to 12 carbon atoms and Hal is F, Cl, Br or I, characterized in that it has a boron content of less than 100 ppb.

Preferred alkylhalohydrosilanes are dimethylchlorosilane and dichloromethylsilane, particular preference being given to dichloromethylsilane.

All above symbols in the above formulae are each defined independently of one another. In all formulae, the silicon atom is tetravalent.

In the context of the present invention, unless stated otherwise in each case, all amounts and percentages are based on weight, all temperatures are 20° C. and all pressures are 1.013 bar (abs.). All viscosities are determined at 25° C.

EXAMPLES

General Synthesis Method

In the process, optionally solvent, alcohol and optionally acid scavenger are initially charged in a flask with stirrer, reflux condenser and dropping funnel; the dropping funnel is used to add organohalohydrosilane dropwise in pure form or in solution. After the addition has ended, reaction is continued for a few hours, the lower phase is removed and discarded, the upper phase is optionally neutralized with metal hydrogencarbonate and filtered, the solvent is drawn off and the organoalkoxyhydrosilane is optionally fractionally distilled.

In the examples, alkylalkoxyhydrosilane= diethoxymethylsilane and alkylhalohydrosilane=dichloromethylsilane, solvent=isohexane, alcohol=ethanol, acid scavenger=urea.

Standard Formulation

All examples are carried out at room temperature 25° C., standard pressure (1.01325 bar).

Example of Formulation

|   |   | [g] or [ml for isohexane] | (%) | (mol) |
|---|---|---|---|---|
| 1 | Dichloromethylsilane | 330.0 | 34.0 | 2.87 |
| 2 | EtOH | 318.0 | 33.0 | 6.90 |
| 3 | Isohexane | 350.0 |  | 2.68 |
| 4 | Urea | 310.0 | 32.0 | 5.17 |

Purification of the Dichloromethylsilane

The boron content in the dichloromethylsilane which is used as the starting material is 890 ppb.

Example 1

Purification of the Methylhydrodichlorosilane by Treatment with Aluminosilicate or Silica As above, the boron content in the methylhydrodichlorosilane is 950 ppb.

Treatment of methylhydrodichlorosilane with x % by weight of aluminosilicate (20 h, nitrogen, room temperature 25° C., standard pressure (1.01325 bar)), stirring and subsequent distillation (no return stream, standard pressure (1.01325 bar), top temperature approx. 40° C.)

starting value see above x % by Weight of Aluminosilicate:

| 0.7% | 90 ppb of boron |
|---|---|
| 2.2% | 60 ppb of boron |
| 5.3% | 30 ppb of boron |

Treatment of methylhydrodichlorosilane with x % by weight of precipitated silica (20 h, nitrogen, room temperature, standard pressure (1.01325 bar), stirring), only filtered (no distillation!)

starting value see above x % by Weight of Precipitated Silica:

| 5% | 130 ppb of boron |
|---|---|
| 10% | 81 ppb of boron |

Example 2

Use of the Methylhydrodichlorosilane Purified by Treatment with Precipitated Silica for Preparing a Methylhydrodiethoxysilane Purification of the Methylhydrodichlorosilane The dichloromethylsilane had been pretreated with 10% by weight of precipitated silica, based on the dichloromethylsilane, and had been distilled.

Preparation of Diethoxymethylsilane

A flask with stirrer, reflux condenser and dropping funnel was initially charged with 318 g of ethanol, 310 g of urea and 350 ml of isohexane; the dropping funnel was used to add dropwise, at room temperature (=25° C.), 330 g of dichloromethylsilane which had been pretreated beforehand as detailed above with 10% by weight of precipitated silica, based on the dichloromethylsilane, and had been filtered. The rate of dropwise addition was selected such that the temperature of 30° C. was not exceeded. After the addition had ended, the reaction was continued at 60° C. for 3 hours. The lower phase was removed and discarded; the upper phase was admixed at room temperature with sufficient sodium hydrogencarbonate to attain a pH of 7. The solution was subsequently filtered, the solvent and excess ethanol were drawn off via a column with 10 trays, and the diethoxymethylsilane was fractionally distilled at a reflux ratio of 1 to 3.

The resulting diethoxymethylsilane had a boron content of 50 ppb of boron.

The invention claimed is:

1. A process for preparing organoalkoxyhydrosilanes with a boron content less than 100 ppb and of the formula $$R^1_x H_y Si(OR^2)_z$$

wherein $x+y+z=4$ and x, y, z are greater than or equal to 1, wherein, in a first step, a boron-contaminated organohalohydrosilane of the formula $$R^1_x H_y SiHal_z$$

wherein $x+y+z=4$, x, y, z are greater than or equal to 1, and $R^1$ are linear or branched alkyl, cycloalkyl, aryl, alkenyl or arylalkyl radicals having 1 to 12 carbon atoms and Hal is F, Cl, Br or I, is subjected to a treatment with silica or aluminosilicate and the silica or the aluminosilicate is subsequently removed from the organohalohydrosilane in a second step and then the purified organohalohydrosilane is reacted with an alcohol $R^2$—OH wherein $R^2$ is a methyl, ethyl, n-propyl, isopropyl, n-butyl, isobutyl, tert-butyl, n-pentyl, isopentyl, neopentyl or tert-pentyl radical.

2. The process for preparing organoalkoxyhydrosilanes according to claim 1, wherein the silica or the aluminosilicate is removed from the organohalohydrosilane by filtration.

3. The process for preparing organoalkoxyhydrosilanes according to claim 1, wherein the silica or the aluminosilicate is removed from the organohalohydrosilane by distillation.

4. The process for preparing organoalkoxyhydrosilanes according to claim 1, wherein at least one solvent is additionally present as well as the alcohol in the course of reaction.

5. The process for preparing organoalkoxyhydrosilanes according to claim 1, wherein at least one acid scavenger is additionally present in the course of reaction.

6. The process for preparing organoalkoxyhydrosilanes according to claim 4, wherein the solvent is isohexane.

7. The process for preparing organoalkoxyhydrosilanes according to claim 5, wherein the acid scavenger is urea.

* * * * *